US008815269B2

(12) United States Patent
Kijlstra et al.

(10) Patent No.: US 8,815,269 B2
(45) Date of Patent: Aug. 26, 2014

(54) INSECTICIDAL FORMULATIONS WITH IMPROVED LONG-TERM EFFECT ON SURFACES

(75) Inventors: Johan Kijlstra, Odenthal (DE); Frank Rosenfeldt, Langenfeld (DE); Guenther Nentwig, Leverkusen (DE); Volker Gutsmann, Langenfeld (DE); Rainer Sonneck, Leverkusen (DE); Douglas Ross, Overland Park, KS (US)

(73) Assignee: Bayer Cropscience AG, Monheim (DE)

( * ) Notice: Subject to any disclaimer, the term of this patent is extended or adjusted under 35 U.S.C. 154(b) by 209 days.

(21) Appl. No.: 12/993,154

(22) PCT Filed: May 19, 2009

(86) PCT No.: PCT/EP2009/003546
§ 371 (c)(1),
(2), (4) Date: Nov. 17, 2010

(87) PCT Pub. No.: WO2009/141109
PCT Pub. Date: Nov. 26, 2009

(65) Prior Publication Data
US 2011/0071228 A1    Mar. 24, 2011

Related U.S. Application Data

(60) Provisional application No. 61/172,265, filed on Apr. 24, 2009.

(30) Foreign Application Priority Data

May 21, 2008  (EP) .................................... 08156623
Jun. 16, 2008  (EP) .................................... 08158297

(51) Int. Cl.
*A01N 25/04* (2006.01)
*A01N 25/00* (2006.01)
*A01N 37/34* (2006.01)

(52) U.S. Cl.
CPC ............. *A01N 25/04* (2013.01); *A01N 25/006* (2013.01); *A01N 37/34* (2013.01)
USPC ............................. 424/405; 424/406; 514/521

(58) Field of Classification Search
None
See application file for complete search history.

(56) References Cited

U.S. PATENT DOCUMENTS

| 2,201,762 | A | * | 5/1940 | Cupery ...................... 525/328.2 |
| 3,400,093 | A |   | 9/1968 | Feinberg |
| 2002/0134012 | A1 | * | 9/2002 | Ding et al. ...................... 47/57.6 |
| 2005/0132500 | A1 | * | 6/2005 | Karl et al. .................... 8/115.51 |
| 2006/0003014 | A1 |   | 1/2006 | Jadhav et al. |
| 2007/0184983 | A1 |   | 8/2007 | Finch et al. |
| 2008/0138371 | A1 |   | 6/2008 | Amrhein et al. |
| 2008/0171658 | A1 |   | 7/2008 | Dyllick-Brenzinger et al. |
| 2008/0213326 | A1 |   | 9/2008 | Amrhein et al. |

FOREIGN PATENT DOCUMENTS

| EP | 1230855 A | 8/2002 |
| WO | 2006006035 A | 1/2006 |
| WO | 2006015791 A | 2/2006 |
| WO | 2006094792 A | 9/2006 |
| WO | 2006094978 A2 | 9/2006 |
| WO | 2007081961 A | 7/2007 |

OTHER PUBLICATIONS

International Preliminary Report on Patentability, Written Opinion, and International Search Report for PCT/EP2009/003546, English language translation, entire document, issued on Jun. 7, 2011.
International Search Report for PCT/EP2009/003546, English language translation, entire document, completed on Mar. 21, 2011.
European Search Report of EP 08156623 dated Aug. 14, 2008.

* cited by examiner

*Primary Examiner* — Neil Levy
(74) *Attorney, Agent, or Firm* — Miles & Stockbridge P.C.

(57) ABSTRACT

The present invention relates to compositions for the control of pests, in particular insecticidal suspension concentrates and spray solutions made from them, to processes for their preparation, and to the use of such formulations for the sustained control of animal pests (arthropods) on a variety of surfaces. The present invention furthermore relates to the use of certain polymer dispersions in pesticides, in particular to their use for extending the long-term activity of these compositions when they are applied to surfaces. The present invention furthermore relates to the use of the compositions according to the invention for controlling parasites, in particular ectoparasites, in animals.

16 Claims, No Drawings

INSECTICIDAL FORMULATIONS WITH IMPROVED LONG-TERM EFFECT ON SURFACES

CROSS REFERENCE TO RELATED APPLICATIONS

This application is a §371 National Stage Application of PCT/EP2009/003546 filed May 19, 2009, which claims priority to U.S. Provisional Application No. 61/172,265 filed Apr. 24, 2009; which claims priority to European Application No. 08158297.5, filed Jun. 16, 2008; which claims priority to European Application No. 08156623.4, filed May 21, 2008.

BACKGROUND OF THE INVENTION

1. Field of the Invention

The present invention relates to compositions for the control of pests, in particular insecticidal suspension concentrates and spray solutions made from them, to a process for their preparation, and to the use of such formulations for the sustained control of animal pests (arthropods) on a variety of surfaces. The present invention furthermore relates to the use of certain polymer dispersions in pesticides, in particular to their use for extending the long-term activity of these compositions when they are applied to surfaces. The present invention furthermore relates to the use of the compositions according to the invention for controlling parasites, in particular ectoparasites, in animals.

2. Description of Related Art

The control of arthropods inside and outside buildings and houses is necessary for a variety of reasons. In countries in which diseases are transmitted by arthropods such as insects or arachnids to animals and humans, for example malaria, there is a great need for protecting the inhabitants in an effective and long-term manner. Moreover, reasons of hygiene and structural engineering require that animal pests be prevented from entering into buildings, spreading and dwelling in buildings and infesting wood or other materials. This is why a multiplicity of control products and methods has already been developed. The most frequently used control method is the application of insecticidally active substances in aqueous spray or atomizing solutions. Independently of the active substance used, the activity of the spray coating will also greatly depend on the physicochemical properties of the sprayed surface. The duration of activity of the spray coating is adversely affected and reduced to a high degree especially on porous and in particular alkaline porous surfaces, such as concrete, render, ashlar/brick, timber (treated and untreated), ceramic, straw or thatch, chalky, limy, gypsiferous, cement-containing and loamy surfaces. In the control of, for example, malaria mosquitoes within buildings, this results in short life-time effects of not more than 6 months.

When controlling pests outside the house, it is the house walls, the soil, the plants and turf areas which are treated. Here, it is not only the surface properties (porosity, pH), but additionally the effects of temperature, UV and rain, which result in the rapid loss of the activity of the active substances employed.

There is a continuous demand for improving the efficacy of the products under these conditions. A longer-term protection can reduce the exposure of the user, the inhabitants, the domestic animals and the environment to a minimum, because active substance needs to be applied less frequently.

SUMMARY OF THE INVENTION

The object on which the present invention is based was therefore the provision of novel, improved insecticidal compositions which offer long-term protection from insects when they are applied to surfaces. It is intended that they be particularly suitable for porous and/or alkaline surfaces and that they be resistant to environmental factors such as high/low/changing temperatures, UV radiation and rain. According to a further aspect, the object also comprises the provision of improved preparations for controlling parasites in animals.

This object is achieved by the compositions according to the invention. Examples of compositions according to the invention are aqueous suspension concentrates, or spray mixtures prepared from them, which generally have a series of advantageous properties. Thus, the compositions according to the invention are solvent-free. Moreover, they are simple to handle and to produce. Upon dilution to the use concentration, they are readily redispersible in water, and, in the spray mixture, only very little sedimentation of the spray mixture takes place. Spray mixtures which can be employed in accordance with the invention can be prepared by diluting a concentrate in water or by mixing various pre-existing solutions directly before spraying (tank-mix application). Compositions according to the invention may also be ready-to-use (RTU) formulations.

The compositions according to the invention contain
- at least one insecticide,
- a nonionic and/or a ionic dispersant,
- an aqueous polymer dispersion, where the polymer dispersion is prepared by polymerization in the presence of a hydrocolloid as the main chain.

The present invention also relates to compositions containing
- at least one insecticide,
- a nonionic and/or ionic dispersant,
- an aqueous polymer dispersion, where the aqueous polymer dispersion is a cationic polymer dispersion, which contains an emulsifier, which has, as the structural component, at least one (meth)acrylic ester and/or (meth)acrylamide, which contains a tertiary amino group.

DETAILED DESCRIPTION OF THE INVENTION

Surprisingly, it has been found that the compositions according to the invention, after application to a surface, show an improved biological long-term activity in comparison with the prior art. This applies in particular to the treatment of porous and in particular alkaline porous surfaces, such as concrete, render, ashlar/brick, timber (treated and untreated), ceramic, straw or thatch, chalky, limy, gypsiferous, cement-containing and loamy surfaces. Here, upon application to nonporous surfaces, the activity remains unaffected on the whole. This is surprising, because a polymer-containing formulation which is suitable for porous surfaces, when applied to nonporous surfaces, usually results in an in-situ encapsulation of the active substance, which drastically reduces the biological activity.

Furthermore, it has surprisingly been found that the durability of the spray coatings obtained by using the aqueous suspension concentrates according to the invention is markedly better than that of previously known coatings, even under the effect of high/low/changing temperatures, rain and UV radiation.

It has furthermore been found, surprisingly, that the compositions according to the invention have proved advantageous on use. Thus, they lead more rarely than prior-art formulations to the clogging of nozzles in the apparatuses used for spraying. Due to the solubility in water, the apparatuses used for applying the compositions according to the invention can be cleaned with particular ease, even after product residues have been left to dry.

The compositions according to the invention preferably contain at least one insecticide selected from among pyrethroids, pyrazoles, neonicotinoids, diamides (anthranilamides, benzenedicarboxamides), carbamates, METI (mitochondrial energy transfer inhibitors (respiratory chain complex I-III), botanical insecticides and inorganic insecticides.

The compositions according to the invention particularly preferably contain at least one insecticide selected from beta-cyfluthrin, cyfluthrin, cypermethrin, alpha-cypermethrin, deltamethrin, bifenthrin, flumethrin, permethrin, lambda-cyhalothrin, gamma-cyhalothrin, metofluthrin, etofenprox, transfluthrin, pyrethrum, indoxacarb, carbaryl, fipronil, metaflumizone, azadirachtin, flubendiamide, chloranthraniliprole, boric acid, borax, imidacloprid, clothianidin, dinotefuran and acetamiprid, fenpyroximate and tolfenpyrad, spinosad.

Besides the abovementioned insecticides, compositions according to the invention may contain further insecticidal active substances, for example selected from alanycarb, aldicarb, aldoxycarb, allyxycarb, aminocarb, bendiocarb, benfuracarb, bufencarb, butacarb, butocarboxim, butoxycarboxim, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate, acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, DDT, nitenpyram, nithiazine, thiacloprid, thiamethoxam, nicotine, bensultap, cartap, spinosad, camphechlor, chlordane, endosulfan, gamma-NCH, HCH, heptachlor, lindane, methoxychlor, acetoprole, ethiprole, pyrafluprole, pyriprole, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine, diafenthiuron, azocyclotin, cyhexatin, fenbutatin-oxide, chlorfenapyr, binapacryl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, *Bacillus thuringiensis* strains, spirodiclofen, spiromesifen, spirotetramat, 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro[4.5]dec-3-en-4-yl ethyl ester, CAS reg. no.: 382608-10-8), flonicamid, amitraz, propargite, thiocyclam hydrogen oxalate, thiosultap-sodium, azadirachtin, *Bacillus* spec., *Beauveria* spec., codlemone, *Metarrhizium* spec., *Paecilomyces* spec., thuringiensin, *Verticillium* spec., aluminium phosphid, methylbromide, sulfurylfluorid, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene and verbutin.

Preference is given to compositions according to the invention with more than one insecticidal active substance beta-cyfluthrin and imidacloprid.

The compositions according to the invention contain an aqueous anionic, cationic or amphoteric polymer dispersion.

Suitable polymer dispersions are preferably finely particulate polymer dispersions which, at a concentration of 0.025% by weight based on the solids content in demineralized water, has an absorbance, measured in a 1 cm cell at 535 nm, of less than 2.0, preferably less than 1.0 and especially preferably less than 0.1.

Preferred polymer dispersions are those which, after drying, have a glass transition temperature of from 0° C. to 120° C., preferably from 25° C. to 90° C. and especially preferably from 40° C. to 80° C.

The glass transition temperature of the polymers was determined as follows. Polymer dispersion which had been left to dry in a DSC pan (drying for 24 hours at room temperature and 0% relative humidity) was determined using the Perkin-Elmer DSC-7 differential scanning calorimeter, equipped with intracooler, over three heating/cooling cycles (−100° C. to +150° C., heating rate 20 K/min, cooling rate 320 K/min, nitrogen flushing with a gas flow rate of 30 ml/min). The glass transition temperature was evaluated at half the level of the glass transition.

The minimum film-formation temperature (MFT) was determined using the Thermostair® temperature gradient testing apparatus (Coesfeld Messtechnik GmbH) as specified in DIN ISO 2115.

To determine the stability to electrolytes of the polymer dispersions, the absorption measurement was carried out as above in parallel after dilution in water and in a $CaCl_2$ dispersion (50 mM). The measurement was carried out 24 hours after preparing the dilution. The relative difference of the two absorption values (water to $CaCl_2$ solution) is a measure for the stability to electrolytes. Polymer dispersions with good stability to electrolytes have a relative absorption difference of less than 20%, preferably less than 5% and especially preferably less than 3%.

Preferred polymer dispersions are those which are obtainable by polymerization of a monomer mixture containing one or more compounds selected from styrene, substituted styrene, acrylonitrile, methacrylonitrile, acrylic ester and (meth) acrylamide.

Examples of acrylic esters which can be employed are methyl acrylate, methyl methacrylate, ethyl acrylate, ethyl methacrylate, propyl acrylate, propyl acrylate, propyl methacrylate, n-butyl acrylate, iso-butyl acrylate, tert-butyl acrylate, n-butyl methacrylate, iso-butyl methacrylate, tert-butyl methacrylate, hexyl acrylate, hexyl methacrylate, ethylhexyl acrylate, stearyl acrylate and stearyl methacrylate. Mixtures of isomeric butyl acrylates are preferred.

Particularly preferred are polymer dispersions which are obtainable by polymerization of a monomer mixture containing an optionally substituted styrene and a $C_1$-$C_4$-alkyl(meth)acrylic ester.

Substituted styrenes which are preferably employed are α-methylstyrene, vinyltoluene or mixtures of these.

Preferred, cationic, aqueous polymer dispersions are obtainable for example by polymerization of a monomer mixture consisting of
a) 20-60% by weight of at least one optionally substituted styrene,
b) 40-80% by weight of at least one $C_1$-$C_{18}$-(meth)acrylic ester and
c) 0-20% by weight of at least one nonionic ethylenically unsaturated monomer other than a) and b),
with the total of a)+b)+c) being 100% by weight,
in the presence of an aqueous polymer dispersion obtainable by a solution polymerization, carried out in a saturated $C_1$-$C_6$-carboxylic acid, of a monomer mixture consisting of
d) 15-35% by weight of at least one (meth)acrylic ester and/or (meth)acrylamide which contains a tertiary amino group,
e) 65-85% by weight of at least one optionally substituted styrene and
f) 0-20% by weight of a nonionic or cationic ethylenically unsaturated monomer other than d) and e),
with the total of d)+e)+f) being 100% by weight.

The cationic polymer dispersion is prepared by emulsion polymerization of a monomer mixture a) to c) in the presence of an aqueous polymer dispersion which acts as emulsifier. The emulsifier, in turn, is prepared by solution polymerization of the monomer mixture d) to f) which is carried out in a saturated $C_1$-$C_6$ carboxylic acid and which, if appropriate, is treated with water after the intermediate isolation and/or work-up.

To prepare the emulsifier, it is preferred to employ, as monomers of group d), (meth)acrylic esters or (meth)acrylamides of the formula (I)

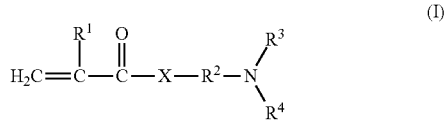

in which
$R^1$ represents H or methyl,
$R^2$ represents a linear $C_1$-$C_4$-alkylene radical,
$R^3$ and $R^4$ are identical or different and represent $C_1$-$C_4$-alkyl and
X represents O or NH.

The monomers of group d) which are employed in particular are compounds which correspond to the formula (I), where $R^3$ and $R^4$ are identical and represent methyl or ethyl. Monomers of group d) which are especially preferably preferred are compounds of the formula (I) where X represents NH and $R^3$ and $R^4$ are identical and represent methyl or ethyl. Monomers of group d) which are very especially preferably employed are those which correspond to the formula (I) where $R^1$ represents H or methyl, $R^2$ represents n-propyl, $R^3$ and $R^4$ are identical and represent methyl and X represents NH.

To prepare the emulsifier, at least one styrene which can optionally be substituted is employed as monomer of group e). From the series of the substituted styrenes, it is preferred to employ α-methylstyrene or vinyltoluene. Unsubstituted styrene is especially preferably employed.

To prepare the emulsifier, the monomers of group f) which are employed are nonionic or cationic, ethylenically unsaturated monomers which are different from d) and e). It is preferred to employ nitriles such as, for example, acrylonitrile or methacrylonitrile, amides such as, for example, acrylamide, methacrylamide or N-methylolacrylamide, vinyl compounds such as, for example, vinyl acetate or vinyl propionate, acrylic acid or methacrylic acid esters of alcohols having 1-18 C atoms such as, for example, methyl acrylate, methyl methacrylate, ethyl acrylate, ethyl methacrylate, propyl acrylate, propyl methacrylate, n-, iso- and tert-butyl acrylate, n-, iso- and tert-butyl methacrylate, hexyl acrylate, hexyl methacrylate, ethylhexyl acrylate, stearyl acrylate and stearyl methacrylate or esters of acrylic acid or methacrylic acid which have been prepared by reaction with at least one ethylene oxide unit, such as, for example hydroxyethyl methacrylate or diethylene glycol monomethacrylate. It is especially preferred to employ, as cationic monomers of group f), vinylpyridine or the quaternized ammonium salts derived from formula (I), which can be obtained for example by reacting compounds of the formula (I) with customary quaternization reagents such as, for example, methyl chloride, benzyl chloride, dimethyl sulphate or epichlorohydrin, such as, for example, 2-(acryloyloxy)ethyltrimethylammonium chloride, 2-(methacryloyloxy)ethyltrimethylammoniumchloride, 3-(acrylamido)propyltrimethylammonium chloride or 3-(methylacrylamido)propyltrimethylammonium chloride.

The parts by weight of the monomers mentioned under d) to f) refer to the total amount of the monomers employed for the preparation of the emulsifier, the total of d)+e)+f) amounting to 100% by weight. It is preferred to employ 20 to 30% by weight of d), 70 to 80% by weight of e) and 0 to 10% by weight of f).

The solution polymerization which is carried out for preparing the emulsifier is carried out as a free-radical polymerization in a saturated $C_1$-$C_6$-carboxylic acid as the solvent. In this context, it is possible to employ not only saturated $C_1$-$C_6$-monocarboxylic acids, but also saturated $C_1$-$C_6$-dicarboxylic acids; it is preferred to employ saturated $C_1$-$C_6$-monocarboxylic acids. The saturated $C_1$-$C_6$-carboxylic acids which are employed optionally have attached to them further substituents such as, for example, hydroxyl groups. The solution polymerization is preferably carried out in formic acid, acetic acid, propionic acid, butyric acid, isobutyric acid, valeric acid, isovaleric acid, caproic acid, hydroxypropionic acid or hydroxybutyric acid. Mixtures of a variety of saturated $C_1$-$C_6$-carboxylic acids can also be employed. It is preferred to carry out the solution polymerization in formic acid, acetic acid, propionic acid or hydroxypropionic acid, especially preferably in acetic acid. In this context, the saturated $C_1$-$C_6$-carboxylic acid employed preferably contains no more than 20% by weight of water, especially preferably no more than 10% by weight of water, very especially preferably no more than 1% by weight of water, based on the total amount of solvent. It is very especially preferred to carry out the solution polymerization in at least 99% strength acetic acid without the admixture of other carboxylic acids. The amount of solvent is chosen such that the concentration of the resulting emulsifier solution is 20 to 70% by weight, calculated from the amount of monomers employed.

The solution polymerization is preferably carried out in the presence of a polymerization regulator. Suitable polymerization regulators are, mainly, sulphur compounds such as, for example, thioglycolic acid or mercaptans such as, for example, ethylmercaptan, n-butylmercaptan, tert-butylmercaptan, n-dodecylmercaptan or tert-dodecylmercaptan. It is preferred to employ mercaptans, especially preferably $C_8$-$C_{14}$-alkylmercaptans.

The solution polymerization is initiated by a free-radical initiator. Free-radical initiators for the solution polymerization which are preferably employed are peroxo or azo compounds such as, for example, hydrogen peroxide, sodium peroxodisulphate, potassium peroxodisulphate and ammonium peroxodisulphate, di-tert-butyl peroxide, dibenzoyl peroxide, azobisisobutyronitrile, 2,2'-azobis(2-methylbutyronitrile), 2,2'-azobis(2,4-dimethylvaleronitrile) or 2,2'-azobis(2-amidino-propane)dihydrochloride. It is preferred to employ azo compounds, especially preferably nitriles such as, for example azobisisobutyronitrile, 2,2'-azobis(2-methylbutyronitrile) or 2,2'-azobis(2,4-dimethylvaleronitrile).

When carrying out the solution polymerization, the amount of free-radical initiator and polymerization regulator is chosen such that an emulsifier with a weight-average molar weight of from 5000 to 100 000 g/mol is obtained. The determination of the molecular weight distribution and of the weight-average molar weight can be carried out by methods known to the skilled worker such as, for example, gel permeation chromatography, light scattering or ultracentrifugation.

After the solution polymerization has ended, the emulsifier obtained is either isolated by intermediate isolation or directly treated with water. It is preferred to treat the emulsifier obtained directly with water and to prepare, by stirring, a homogeneous liquid phase in which the emulsifier is present in partially dissolved and partially dispersed form. The concentration of the emulsifier in the liquid phase after the addition of water is preferably 2 to 20% by weight, especially preferably 5 to 15% by weight. This liquid phase can be employed directly for carrying out the emulsion polymerization for the preparation of the cationic finely-divided aqueous polymer dispersion.

The cationic aqueous polymer dispersion is prepared by emulsion polymerization of a monomer mixture consisting of a) to c), where the aqueous polymer dispersion prepared in the first step acts as the emulsifier.

To prepare the cationic aqueous polymer dispersion, the monomers of group a) which are employed are styrene and/or substituted styrenes such as, for example, α-methylstyrene or vinyltoluene. It is especially preferred to employ unsubstituted styrene.

To prepare the cationic aqueous polymer dispersion, the monomers of group b) which are employed are at least one $C_1$-$C_{18}$-(meth)acrylic acid ester. It is preferred to employ methacrylate, methyl methacrylate, ethyl acrylate, ethyl methacrylate, propyl acrylate, propyl methacrylate, n-, iso- and tert-butyl acrylate, n-, iso- and tert-butyl methacrylate, hexyl acrylate, hexyl methacrylate, ethylhexyl acrylate, stearyl acrylate and stearyl methacrylate. It is especially preferred to employ n-butyl acrylate or binary mixtures which contain between 10 and 90% by weight of n-butyl acrylate. It is very especially preferred to employ mixtures of n-butyl acrylate and tert-butyl acrylate.

To prepare the cationic aqueous polymer dispersion, the monomers of group c) which are employed are at least one nonionic, ethylenically unsaturated monomer other than a) and b). It is preferred to employ nitriles such as, for example, acrylonitrile or methacrylonitrile, amides such as, for example, acrylamide, methacrylamide or N-methylolacrylamide, vinyl compounds such as, for example, vinyl acetate or vinyl propionate, dienes such as, for example, butadiene or isoprene, and esters of acrylic acid or methacrylic acid and at least one ethylene oxide unit such as, for example, hydroxyethyl methacrylate or diethylene glycol monomethacrylate.

The concentration of the cationic aqueous polymer dispersion is preferably from 10 to 40% by weight, especially preferably from 15 to 35% by weight. The viscosity of a 20% dispersion is, as a rule, 3 to 30 mPas, measured at a temperature of 23° C. The mean particle size of a 20% dispersion is preferably <100 nm, it is especially preferably from 5 to 50 nm. The mean particle size can be determined by methods known to the skilled worker such as, for example, laser correlation spectroscopy, ultracentrifugation or turbidimetry.

A particularly preferred embodiment of the invention is the use of aqueous polymer dispersions obtainable by polymerization of a monomer mixture in the presence of a hydrocolloid as the main chain.

Hydrocolloids are macromolecular, hydrophilic substances which are soluble or dispersible in water and swellable, giving rise to viscous solutions, gels or stabilized systems, such as, for example, agar, carrageenan, xanthan, gellan, galactomannans, gum arabic, tragacanth, karaya, curdlan, beta-glucan, alginates, mannans, chitosan, celluloses, proteins, gelatin, pectin, starch, and their modified and/or degraded (for example hydrolyzed and/or oxidized) forms, and synthetic water-soluble polymers. The preferred hydrocolloid is degraded starch.

Such grafted aqueous polymer dispersions can be obtained for example by radical-initiated emulsion copolymerization of ethylenically unsaturated monomers in the presence of starch, characterized in that the ethylenically unsaturated monomers employed are (a) 30 to 60% by weight of at least one optionally substituted styrene,
(b) 60 to 30% by weight of at least one $C_1$-$C_4$-alkyl(meth)acrylate,
(c) 0 to 10% by weight of other ethylenically unsaturated copolymerizable monomers, the starch (d) employed is 10 to 40% by weight of degraded starch with a molar weight $M_n$=500 to 10 000, the total of (a)+(b)+(c)+(d) being 100%,
and the free-radical-initiator employed for the radical-initiated emulsion polymerization is a graft-active, water-soluble redox system.

Suitable monomers a) to c) are the compounds already disclosed for the cationic polymer dispersion.

The grafted polymer dispersions have a particle size below 100 nm, preferably of 50 to 90 nm.

The present invention also relates to the use of the aqueous polymer dispersions according to the invention in pesticides. In this context, they are used as described in the present application and as substantiated by examples.

The compositions according to the invention contain nonionic and/or ionic dispersants.

Examples of suitable nonionic surfactants are polyethylene oxide/polypropylene oxide block copolymers, polyethylene glycol ethers of linear alcohols, reaction products of fatty acids with ethylene oxide and/or propylene oxide, furthermore polyvinyl alcohol, polyvinylpyrrolidone, mixed polymers of polyvinyl alcohol and polyvinylpyrrolidone, and copolymers of (meth)acrylic acid, (meth)acrylic esters, furthermore alkyl ethoxylates and alkylaryl ethoxylates which may optionally be phosphated and optionally be neutralized with bases, examples which may be mentioned being sorbitol ethoxylates.

Ionic dispersants which are preferably employed are anionic dispersants, for example modified sodium lignosulphonates, Kraft sodium lignosulphonates, naphthalene-formaldehyde condensates, polyaspartic acid, polyacrylates, polyethylene sulphonates, modified starch, gelatin, gelatin derivatives or anionic surfactants (such as, for example, aromatic or aliphatic sulphates and sulphonates, or sulphated or sulphonated aromatic or aliphatic ethoxylates).

In the case of finely distributed active substance particles, or active-substance-containing carrier particles, it is particularly preferred to use anionic and/or nonionic dispersants.

Besides the abovementioned components, the compositions according to the invention optionally contain
 a thickener (optionally including thickening activator),
 a preservative,
 an antifoam,
 one or more acids or bases in such an amount as to adjust the pH of the mixture in a targeted manner, or to activate thickener, and
 further components for optimizing the use properties of the formulation.

Suitable thickeners are all the substances which act as thickeners and which can conventionally be employed for this purpose in agrochemical compositions. Preferred substances are inorganic particles such as carbonates, silicates and oxides, and also organic substances such as urea/formaldehyde condensates. Examples which may be mentioned are kaolin, rutile, silicon dioxide, what is known as highly disperse silica, silica gels, and also natural and synthetic silicates, furthermore talc. Thickeners which can furthermore be employed are synthetic thickeners such as polyacrylate thickeners (for example Carbopol® and Pemulen® thickeners from Lubrizol, Cleveland, USA), biological thickeners (for example Kelzan® S, xanthan gum, or further hydrocolloids from CP Kelco, Atlanta, USA) and inorganic thickeners (for example layer silicates such as kaolin, montmorillonite and laoponite).

Preservatives which are suitable are all substances which can be employed for this purpose in agrochemical compositions of this type. Examples which may be mentioned are Preventol® (Lanxess AG) and Proxel® (Arch Chemival, Inc.).

Antifoams which are suitable are all substances which can be employed for this purpose in agrochemical compositions. Silicone oils and magnesium stearate are preferred.

The amount of active substance in the compositions according to the invention can be varied within a wide range. In the case of concentrated formulations, for example aqueous suspension concentrates, it is generally between 0.01 and 40% by weight, preferably between 0.1 and 20% by weight, preferably between 1 and 20% by weight and especially preferably between 1 and 10% by weight.

The amount of polymer can also be varied within a wide range. In concentrated formulations, it is generally between 1 and 50% by weight, preferably between 2 and 40% by weight and especially preferably between 6 and 20% by weight. In this context, the amounts specified indicate the content based on the solids content. Frequently, it is in the form of an aqueous dispersion that the polymers are synthesized, or offered for sale, and employed for preparing the compositions according to the invention.

The amount of active substance in ready-to-use compositions according to the invention can be varied within a wide range. In the case of ready-to-use formulations, it is generally between 0.001 and 0.5% by weight, preferably between 0.01 and 0.1% by weight.

The amount of polymer in ready-to-use compositions according to the invention can also be varied within a wide range. In ready-to-use formulations, it is generally between 0.002 and 1% by weight, preferably between 0.004 and 0.8% by weight and especially preferably between 0.01 and 0.4% by weight. In this context, the amounts specified indicate the content based on the solids content. Frequently, it is in the form of an aqueous dispersion that the polymers are offered for sale, and employed for preparing the compositions according to the invention.

The suspension concentrates according to the invention are prepared in such a way that the components are mixed with one another in the ratios desired in each case. The sequence in which the components are mixed with one another is of no importance; however, it is usual to add the thickener last of all. The solid components are expediently employed in a finely-ground state. However, it is also possible to subject the suspension obtained after mixing the components first to coarse milling and then to fine milling, so that the main particle size is, for example, below 5 μm.

When carrying out the process according to the invention, the temperatures can be varied within a certain range. Suitable temperatures are between 10° C. and 60° C., preferably between 15° C. and 40° C. Customary mixing and grinding equipment which is employed for the preparation of agrochemical formulations is suitable for carrying out the process according to the invention.

It is also possible to use active substance particles, or active-substance-containing particles and/or granules, which have been obtained for example via spray drying, spray solidification or fluidized-bed processes (for example as described in EP 1 324 661). These are usually coarsely particulate, i.e. for example with a mean particle size d50 greater than 5 μm (determined after dispersion in the water phase by means of laser diffraction).

The formulations according to the invention can be used successfully for destroying harmful arthropods or nuisance arthropods, in particular arachnids and insects.

The arachnids include mites (for example *Sarcoptes scabiei, Dermatophagoides pteronyssinus, Dermatophagoides farinae, Dermanyssus gallinae, Acarus siro*) and ticks (for example *Ixodes ricinus, Ixodes scapularis, Argas reflexus, Ornithodorus moubata, Rhipicephalus (Boophilus) microplus, Amblyomma hebraeum, Rhipicephalus sanguineus*).

The sucking insects include essentially the mosquitoes (for example *Aedes aegypti, Aedes vexans, Culex quinquefasciatus, Culex tarsalis, Anopheles albimanus, Anopheles stephensi, Mansonia titillans*), the moth gnats (for example *Phlebotomus papatasii*), gnats (for example *Culicoides furens*), buffalo gnats (for example *Simulium damnosum*), stinging flies (for example *Stomoxys calcitrans*), tsetse flies (for example *Glossina morsitans morsitans*), horse flies (for example *Tabanus nigrovittatus, Haematopota pluvialis, Chrysops caecutiens*), true flies (for example *Musca domestica, Musca autumnalis, Musca vetustissima, Fannia canicularis*), flesh flies (for example *Sarcophaga carnaria*), myiasis-causing flies (for example *Lucilia cuprina, Chrysomyia chloropyga, Hypoderma bovis, Hypoderma lineatum, Dermatobia hominis, Oestrus ovis, Gasterophilus intestinalis, Cochliomyia hominivorax*), bugs (for example *Cimex lectularius, Rhodnius prolixus, Triatoma infestans*), lice (for example *Pediculus humanis, Haematopinus suis, Damalina ovis*), fleas (for example *Pulex irritans, Xenopsylla cheopis, Ctenocephalides canis, Ctenocephalides felis*) and sand fleas (*Tunga penetrans*).

The biting insects include essentially cockroaches (for example *Blattella germanica, Periplaneta americana, Blatta orientalis, Supella longipalpa*), beetles (for example *Sitiophilus granarius, Tenebrio molitor, Dermestes lardarius, Stegobium paniceum, Anobium punctatum, Hylotrupes bajulus*), termites (for example *Reticulitermes lucifugus*), ants (for example *Lasius niger, Monomorium pharaonis*), wasps (for example *Vespula germanica*) and larvae of moths (for example *Ephestia elutella, Ephestia cautella, Plodia interpunctella, Hofmannophila pseudospretella, Tineola bisselliella, Tinea pellionella, Trichophaga tapetzella*).

The materials according to the invention are preferably employed against insects, mainly from the orders Diptera and Dictyoptera.

Unless the compositions according to the invention are present in ready-to-use form (for example as aqueous suspension concentrate), they are first diluted in water for their intended use. In this context, the compositions are diluted to such an extent that the active substance content, with the intended application rate, ensures sufficient insecticidal activity. Here, the dilution gives compositions which correspond to the above-specified ready-to-use compositions.

The diluted spray solution can be sprayed in any customary manner, for example by hand-operated or electrical sprayers.

In this context, the active substance is generally applied at an application rate of from 1 to 1000 mg/m$^2$, preferably at an application rate of from 1 to 500 mg/m$^2$, especially preferably at an application rate of from 5 to 250 mg/m$^2$ and very especially preferably at a concentration of from 10 to 250 mg/m$^2$.

The compositions according to the invention are preferably applied at such a dilution rate and application rate to a surface that the polymer is applied at a deposition rate (based on solid) of from 1.0 mg/m$^2$ to 2000 mg/m$^2$, preferably from 5.0 mg/m$^2$ to 500 mg/m$^2$, especially preferably from 5 mg/m$^2$ to 200 mg/m$^2$ and especially preferably from 10 mg/m$^2$ to 200 mg/m$^2$ The compositions according to the invention can be applied to any surface inside buildings or in the open, for example wallpaper, concrete, render, ashlar, timber (treated and untreated), ceramic (glazed and unglazed), straw or thatch, brick (untreated, limewashed, painted), clay minerals (for example terracotta), chalky, limy, gypsiferous, cement-containing and loamy surfaces.

The preparations according to the invention can also be employed in the animal health sector, i.e. in the field of veterinary medicine, mainly for the control of parasites, in particular ectoparasites, in animals. Ectoparasites are typically and preferably arthropods, in particular insects such as flies (stinging and licking), parasitic fly larvae, lice, chewing lice, bird lice, fleas and the like; or acarids such as ticks, for example hard ticks or soft ticks, or mites such as scab mites, harvest mites, bird mites and the like.

These parasites include:

From the order Anoplurida, for example *Haematopinus* spp., *Linognathus* spp., *Pediculus* spp., *Phtirus* spp., *Solenopotes* spp.; from the order Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order Siphonapterida for example *Pulex* spp., *Ctenocephalides* spp., *Tunga* spp., *Xenopsylla* spp., *Ceratophyllus* spp.; from the subclass Acari (Acarina) and the orders Meta- and Mesostigmata, for example *Argas* spp., *Ornithodorus* spp., *Otobius* spp., *Ixodes* spp., *Amblyomma* spp., *Rhipicephalus* (*Boophilus*) spp. *Dermacentor* spp., *Haemophysalis* spp., *Hyalomma* spp., *Dermanyssus* spp., *Rhipicephalus* spp. (the original genus of multiple-host ticks), *Ornithonyssus* spp., *Pneumonyssus* spp., *Raillietia* spp., *Sternostoma* spp., *Varroa* spp., *Acarapis* spp.; from the order Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The preparations according to the invention are preferably employed in veterinary medicine for controlling the following parasites:

Flies (order Diptera), in particular horn flies, (for example *Haematobia irritans*), stable flies (for example *Stomoxys calcitrans*), face flies (for example *Musca autumnalis*), house flies (for example *Musca domestica*), blow flies (myiasis-causing flies, family Calliphoridae), mosquitoes (family Culicidae), black flies (family Simuliidae), gnats (*Culicoides* spp.), sand flies (*Phlebotomus* spp.).

Lice, in particular biting lice (chewing lice, order Mallophaga), sucking lice (order Anoplura);

Ticks, in particular hard ticks (family Ixodidae), for example *Ixodes ricinus, I. scapularis, Amblyomma americanum, A. hebraeum, Rhipicephalus sanguineus, Rhipicephalus* (*Boophilus*) *microplus, R.* (*B.*) *decoloratus, Dermacentor variabilis, D. reticulates, Haemophysalis leachi, Hyalomma anatolicum*; soft ticks (family Argasidae), for example *Argas reflexus, Ornithodorus moubata*;

Mites, in particular mesostigmatous mites, for example *Dermanyssus gallinae, Ornithonyssus sylviarum*; pro- and astigmatous mites, for example *Demodex canis, Neotrombicula autumnalis, Otodectes cynotis, Notoedres cati, Sarcoptis canis, Sarcoptes bovis, Sarcoptes ovis, Sarcoptes suis, Psoroptes ovis*.

Of course, the precise spectrum of action of the preparations according to the invention will depend on the active substances employed.

In preparations for use in veterinary medicine, the following active substances are especially preferred, inter alia:

Neoncotinoids, such as, for example, clothianidin, imidacloprid, thiacloprid; pyrethroids, such as, for example, cyfluthrin, beta-cyfluthrin; organo(thio)phosphates such as, for example, coumaphos; pyrazoles such as, for example, fenpyroximate or tolfenpyrad; pyrroles such as, for example, chlorofenapyr, and carbamate insecticides such as, for example, indoxacarb.

The preparations according to the invention are preferably suitable for controlling ectoparasitic arthropods which attack animals. The animals include agricultural livestock such as, for example, cattle, sheep, goats, horses, pigs, donkeys, camels, buffalos, rabbits, chickens, turkeys, ducks, geese, farmed fish. The animals furthermore include domestic animals—also referred to as pets—such as, for example, dogs, cats, cage birds, aquarium fish, and what are known as experimental animals such as, for example, hamsters, guinea pigs, rats and mice. Preferred domestic animals are cats or dogs.

Furthermore preferred is the use in horses.

Especially preferred is the use in sheep, goats or in particular in cattle or pigs.

By controlling these parasites, it is intended to reduce deaths and to increase the performance (as regards meat, milk, wool, hides, eggs, honey and the like) and the health of the host animal, so that, by employing the active substances according to the invention, more economical, simpler and better animal keeping is possible.

Thus, for example, it is desirable to prevent or minimize the uptake of host blood by the parasites (in as far as this applies to the parasite in question). Moreover, controlling the parasites may contribute to preventing the transmission of infectious pathogens.

The term "control", in as far as it is used in the present context with reference to the animal health sector, means that the preparations act by reducing the occurrence of the parasite in question in an animal infested with such a parasite to a harmless level. More precisely, "control" as used in the present context means that the preparation destroys the parasite in question or inhibits its growth or its proliferation.

In general, the preparations according to the invention, when employed for the treatment of animals, can be used directly. They are preferably used as pharmaceutical preparations which may contain further pharmaceutically acceptable excipients and/or adjuvants which are known in the art.

The use (=administration) of the preparations in the animal health sector and in animal keeping is carried out in a manner known per se, preferably by external use in the form of, for example, dipping or bathing, spraying, pouring-on and spotting-on, washing and the like. To this end, the preparations can be formulated for example as pour-on formulations, spot-on formulations, as a shampoo or spray, such as aerosols or nonpressurized sprays (for example pump sprays and atomizer sprays).

When used in the animal health sector, the preparations according to the invention may contain active substance combinations with suitable synergists or further active substances such as, for example, acaricides or insecticides.

PREPARATION EXAMPLES

Example 1

In a flask equipped with stirrer, reflux condenser and heating jacket, 124.5 g of oxidatively degraded potato starch are dispersed under nitrogen in 985 g of deionized water and dissolved by warming. In succession, 42.7 g of a 1% strength iron(II) sulphate solution and 116 g of a 3% strength hydrogen peroxide solution are added, and the mixture is stirred for 15 min at 86° C. After 15 minutes, the following two metering solutions are metered in simultaneously, but separately with constant dosing rate within 90 min at 86° C.:
1) 321 g of a mixture of styrene, n-butyl acrylate and tert-butyl acrylate
2) 93.7 g of a 3% strength hydrogen peroxide solution.

After all of the solutions have been metered in, stirring is continued for 15 min at 86° C., and 2 g of t-butyl hydroperoxide are then added to let the mixture afterreact. After a further 60 min at 86° C., the mixture is cooled to room temperature, 10 g of a 10% strength solution of EDTA in the form of the tetrasodium salt are added, and a pH of 6.5 is adjusted with 13 g of a 10% strength sodium hydroxide solution. The mixture is passed through a 100 μm filter cloth, giving a finely divided dispersion with a solids content of 24.0% by weight.

The ratio between styrene, n-butyl acrylate and tert-butyl acrylate can be varied, depending on the desired polymer properties (glass transition temperature, minimum film-forming temperature). The suitable ratio can be determined experimentally following the above protocol.

BIOLOGICAL EXAMPLES

Example A

A polymer dispersion (hereinbelow referred to as PD-SACP) was prepared in accordance with the above Preparation Example 1. The monomer composition was adjusted in such a way that the polymer had a glass transition temperature of 50° C. and a minimum film-forming temperature of 44° C. The turbidity value of the dispersion, diluted to 0.025% by weight, was E=0.02 (535 nm, 1 cm cell). The dilution medium used was demineralized water. However, comparative measurements with a 50 mM solution of $CaCl_2$ solution gave identical absorbance values.

Two spray solutions, FL1 and FL2, were prepared as follows:

TABLE 1

Composition spray solutions

| | FL1 % by weight | FL2 % by weight |
|---|---|---|
| Crackdown ® SC 10 (Bayer CropScience AG) | 7.14 | 7.14 |
| PD-SACP | — | 0.60 |
| Water | 92.86 | 92.26 |

These solutions were sprayed onto a concrete surface at an application rate of 25 mg deltamethrin per $m^2$, using a fan nozzle (type SS 8003 E). The application rate for the spray solutions was, therefore, 35 ml/$m^2$. To make the concrete surface, the dry mortar Weber.mix 604 (Saint-Gobain Weber GmbH) was mixed with water in accordance with the manufacturer's instructions, stirred, poured into Petri dishes to harden (diameter 13.5 cm, height 2 cm) and subsequently stored for at least 3 weeks.

The treated surfaces were then stored at 35° C. and 80% relative atmospheric humidity and tested after 2 weeks' storage.

To this end, the mosquitoes (*Culex quinquefasciatus*), which had been stunned with carbon dioxide were placed centrally on the treated surfaces and covered with an aluminium ring provided with gauze (mosquitoes). The exposure time was 24 hours. During the exposure, the temperature was 24-26° C., the atmospheric humidity was not controlled. After 0.5, 1, 2, 4 and 6 hours, the knock-down effect was registered, and, after 24 hours, the mortality. Each test consisted of 3 replications, of which the mean was formed. Table 2 shows the results.

TABLE 2

Effect against *Culex quinquefasciatus* of Crackdown ® SC 010 without (FL1) and with PD-SACP (FL2) after 2 weeks' storage

| | Reading | |
|---|---|---|
| (h) | FL1 % knock-down/mortality | FL2 % knock-down/mortality |
| 0.5 | 0 | 0 |
| 1 | 0 | 0 |
| 2 | 3 | 0 |
| 4 | 3 | 0 |
| 6 | 15 | 25 |
| 24 | 45 | 95 |

It is surprising that the active substance dispersion with PD-SACP shows better results than the active substance dispersion without polymer dispersion.

Example B

A series of spray solutions FL3 to FL8 based on Responsar® SC 025 (Bayer CropScience AG, containing 25 g/l beta-cyfluthrin) were made up as follows:

TABLE 3

Composition spray solutions FL3 to FL8

| | FL3 % by weight | FL4 % by weight | FL5 % by weight | FL6 % by weight | FL7 % by weight | FL8 % by weight |
|---|---|---|---|---|---|---|
| Responsar ® SC 025 | 2.86 | 2.86 | 2.86 | 2.86 | 2.86 | 2.86 |
| PD-SACP | — | 0.14 | 0.29 | 0.59 | 0.89 | 1.19 |
| Water | 97.14 | 97.00 | 96.85 | 96.55 | 96.25 | 95.95 |

The biological effect of these formulations was tested on concrete slabs analogously to Example A. The application rate of beta-cyfluthrin was 25 mg per $m^2$.

Table 4 shows the results.

TABLE 4

Effect against *Culex quinquefasciatus* of Responsar ® SC 025 without (FL3) and with increasing concentrations of PD-SACP (FL4-FL8) after 2 weeks' storage

| (h) | FL3 % knock-down/mortality | FL4 % knock-down/mortality | FL5 % knock-down/mortality | FL6 % knock-down/mortality | FL7 % knock-down/mortality | FL8 % knock-down/mortality |
|---|---|---|---|---|---|---|
| 0.5 | 2 | 5 | 0 | 0 | 2 | 7 |
| 1.0 | 2 | 3 | 0 | 20 | 13 | 22 |
| 2.0 | 3 | 23 | 0 | 83 | 40 | 47 |
| 4.0 | 12 | 63 | 38 | 100 | 95 | 93 |
| 6.0 | 42 | 93 | 88 | 100 | 98 | 100 |
| 24 | 75 | 97 | 98 | 100 | 100 | 100 |

It is surprising that the biological effect of beta-cyfluthrin is increased markedly by addition of PD-SACP.

Example C

A deltamethrin suspension concentrate with and without PD-SACP was prepared by fine-milling in a bead mill, as follows:

TABLE 5

Composition of the suspension concentrates FL9 and FL10

| | FL9 % by weight | FL10 % by weight |
|---|---|---|
| Deltamethrin | 3.00 | 3.00 |
| Soprophor FLK (Rhodia) | 0.18 | 0.18 |
| Emulgator PS 29 (Tanatex Chemicals) | 0.18 | 0.18 |
| Citric acid | 0.02 | 0.02 |
| Kelzan (CP Kelco) | 0.06 | 0.06 |
| PD-SACP | — | 25.00 |
| Water | 96.57 | 71.57 |

Both formulations were diluted in water (to 0.07% by weight deltamethrin) and sprayed onto concrete slabs (Weber.mix 604) analogously to Example A (application rate 25 mg deltamethrin per $m^2$), and subjected to biotests (after one week's storage at 35° C. and 80% relative atmospheric humidity). Table 6 shows the results.

TABLE 6

Effect against *Culex quinquefasciatus* of deltamethrin suspension concentrate without (FL9) and with PD-SACP (FL10) after 2 weeks' storage.

| | Reading | |
|---|---|---|
| h | FL9 % knock-down/mortality | FL10 % knock-down/mortality |
| 0.5 | 0 | 0 |
| 1 | 0 | 0 |
| 2 | 3 | 0 |
| 4 | 3 | 15 |
| 6 | 3 | 32 |
| 24 | 15 | 100 |

It can be seen that the formulation according to the invention shows better results than the suspension concentrate without PD-SACP.

Example D

A deltamethrin suspension concentrate with and without PD-SACP was prepared by fine-milling in a bead mill, as follows:

TABLE 7

| Composition suspension concentrate FL11 | FL11 % by weight |
|---|---|
| Deltamethrin | 3.00 |
| Dispersogen SI (Clariant) | 1.80 |
| Rhodopol 23 (Rhodia) | 0.08 |
| Citric acid | 0.02 |
| Agnique SLS 90P (Cognis) | 0.01 |
| PD-SACP | 25.00 |
| Water | 95.09 |

Deltamethrin dispersions (0.07% by weight deltamethrin) in water were prepared with the formulation FL11 and the commercially available granules K-Othrine® WG 250 (Bayer CropScience AG, containing 25% by weight deltamethrin) and sprayed onto different concrete slabs (Weber.mix 601 or 604) analogously to Example A (application rate 25 mg deltamethrin per $m^2$), and subjected to biotests (after two weeks' storage at 35° C. and 80% relative atmospheric humidity). Table 8 shows the results.

TABLE 8

Effect against *Culex quinquefasciatus* of deltamethrin suspension concentrate with PD-SACP (FL11) and of K-Othrine ® WG 250 without PD-SACP after 2 weeks' storage

| | Substrate | | | |
|---|---|---|---|---|
| | Weber. mix 601 | | Weber. mix 604 | |
| Reading | | | | |
| (h) | FL11 % knock-down/mortality | K-Othrine ® WG 250 % knock-down/mortality | FL11 % knock-down/mortality | K-Othrine ® WG 250 % knock-down/mortality |
| 0.5 | 0 | 0 | 0 | 0 |
| 1 | 2 | 0 | 7 | 3 |
| 2 | 3 | 2 | 53 | 10 |
| 4 | 17 | 8 | 92 | 33 |
| 6 | 53 | 22 | 100 | 57 |
| 24 | 92 | 95 | 100 | 100 |

It can be seen that the formulation according to the invention shows better results than K-Othrine® WG 250, although the last-mentioned product is designed specifically for the long-term impregnation of surfaces with deltamethrin.

Example E

Aqueous polymer dispersions based on styrene/(meth) acrylate copolymers were prepared analogously to Preparation Example 1 by radical-initiated emulsion polymerization, using different monomer compositions. In this manner, the polymer dispersions PD1 to PD6 with a solids content of 24% by weight and different glass transition temperatures and minimum film-forming temperatures were obtained (see Table 9).

The turbidity of the polymer dispersions was characterized by absorption measurement in an aqueous dispersion with a solids content of 0.025% by weight (1 cm cell, 535 nm). The dilution medium used was demineralized water. However, comparative measurements with a 50 mM $CaCl_2$ solution gave identical absorbance values.

TABLE 9

Physical data

| Polymer dispersion | Glass transition temperature (° C.) | Minimum film-forming temperature (° C.) | Absorbance (—) |
|---|---|---|---|
| PD 1 | 50 | 44 | 0.019 |
| PD 2 | 34.5 | 27 | 0.014 |
| PD 3 | 78.5 | 70 | 0.019 |
| PD 4 | 22.5 | 13 | 0.015 |
| PD 5 | 37 | 28 | 0.016 |
| PD 6 | 52.5 | 47 | 0.025 |

Analogously to formulation FL11 of Example D, suspension concentrates with deltamethrin and in each case one of the polymer dispersions PD1 to PD6 (as replacement for PD-SACP) were prepared and subjected to biotests on concrete slabs (Weber.mix 604) (storage of the concrete slabs at 35° C. and 80% relative atmospheric humidity for up to 2 weeks; evaluation of the mortality after 24 h). By way of reference, the formulation. FL11 of Example D was made up without polymer dispersion by adjusting the water content and subjected to biotests. Table 10 shows the results.

TABLE 10

Effect against *Culex quinquefasciatus* of deltamethrin suspension concentrate with different polymer dispersions after storage for 1 day, 1 week and 2 weeks

| | Storage | | |
|---|---|---|---|
| | 1 day % mortality (24 h) | 1 week/35° C. % mortality (24 h) | 2 weeks/35° C. % mortality (24 h) |
| PD 1 | 100 | 98 | 67 |
| PD 2 | 100 | 85 | 38 |
| PD 3 | 100 | 98 | 67 |
| PD 4 | 100 | 80 | 35 |
| PD 5 | 100 | 78 | 32 |
| PD 6 | 100 | 93 | 60 |
| Reference without polymer dispersion | 100 | 57 | 20 |

It is surprising that the biological effect is improved with the formulations according to the invention.

Example F

The commercial product Tempo® Ultra SC (active substance beta-cyfluthrin) was diluted with water as described in the instructions. The finished spray solution was treated with PD-SACP up to 0.5% by weight. These finished spray solutions were applied to timber planks at an application rate of 40 ml per m². The planks treated thus were infested with insects (Acheta), and the mortality was determined. Between the measurements, the treated planks were stored in the open with exposure to sun and rain.

TABLE 11

Effect against house crickets (*Acheta domesticus*) of Tempo ® Ultra (Bayer CropScience AG) without and with PD-SACP on spruce timber after 56 days' storage in the open (average temperature 26° C., precipitation 300 mm)

| (min) | Tempo ® Ultra % mortality | Tempo ® Ultra & PD SACP % mortality |
|---|---|---|
| 15 | 0 | 0 |
| 30 | 0 | 0 |
| 45 | 0 | 0 |
| 60 | 5 | 40 |
| 90 | 20 | 60 |
| 120 | 25 | 90 |
| 180 | 38 | 95 |

The biological effect against crawling insects is improved by the formulation according to the invention, even under the effect of rain and light.

Example G

The commercial product Temprid® (active substance mixture of beta-cyfluthrin and imidacloprid) was diluted with water as described in the instructions. The finished spray solution was treated with PD-SACP up to 0.5% by weight. These finished spray solutions were applied to glazed tiles at an application rate of 40 ml per m². The tiles treated thus were infested with insects (*Blattella*), and the mortality was determined. Between the measurements, the treated tiles were stored in the open with exposure to sun and rain.

TABLE 12

Effect against German cockroaches (*Blattella germanica*) of Temprid ® (Bayer CropScience AG) without and with PD-SACP on tiles after storage in the open (average duration of sunshine 4.3 h/d, precipitation 170 mm) for the stated number of days (d).

|  | 1 d | 14 d | 28 d | 56 d | 112 d |
|---|---|---|---|---|---|
| Temprid ® | 100 | 70 | 0 | 0 | 0 |
| Temprid ® & PD SACP | 100 | 70 | 40 | 100 | 90 |

The data shown are the mortality after 24 h and 30 min exposure of the insects on the treated surfaces.

The biological activity of active substance mixtures is improved by the formulation according to the invention.

Example H

The effect on *Haematobia irritans* (horn fly) in cattle of a preparation with polymer addition in comparison with a preparation without polymer addition was tested in a field experiment.

For the comparative preparation "A", the commercial product Poncho 600® (product for seed treatment, SC with 48% clothianidin) was diluted with water to an active substance content of 6%. This mixture was applied externally to the backs of cattle at a dose of 10 mg active substance/kg body weight (100 ml per animal).

For the preparation "B", the commercial product Poncho 600® was diluted with water to an active substance content of 6%, and 29.5 ml/l S.A.C.P. were then added. This mixture was applied externally to the backs of cattle at a dose of 10 mg active substance/kg body weight (100 ml per animal). The cattle were divided into three treatment groups: control group: untreated (10 animals); group A: treated with preparation A (5 animals), group B: treated with preparation B (5 animals).

Regimen: on day 0 (10 am to 12 pm), the flies on all animals were counted, and groups a and B were then treated immediately as stated. On the same day (3 pm to 4 pm) and on the following days (see table) the flies were counted again.

During the study, it rained on day 5 (after the flies were counted), on days 13 to 15, on day 16 (after the flies were counted) and on days 20, 21. It emerged that the effect of preparation B is less influenced by the rain than that of preparation A.

TABLE 13

Experiments on the control of horn flies in cattle
Clothianidin cattle pour-on - control of horn flies in cattle

| Treatment group | Average number of flies/animal | | | | | | | | |
|---|---|---|---|---|---|---|---|---|---|
| | Day 0 bef. tr.* | Day 0 aft. tr.* | Day 2 | Day 5 | Day 9 | Day 13 | Day 16 | Day 19 | Day 24 |
| Untreated control group | 389 | 347 | 346 | 394 | 339 | 301 | 336 | 209 | 43 |
| Group A (clothianidin) | 462 | 6 | 4 | 3 | 27 | 157 | 174 | 164 | 72 |
| Group B (clothianidin + PD SACP) | 350 | 2 | 1 | 2 | 2 | 9 | 42 | 28 | 8 |

| | % effect (based on the untreated control group) | | | | | | | |
|---|---|---|---|---|---|---|---|---|
| Untreated (control) | Day 0 aft. tr.* | Day 2 | Day 5 | Day 9 | Day 13 | Day 16 | Day 19 | Day 24 |
| Group A (clothianidin) | 98% | 99% | 99% | 92% | 48% | 48% | 21% | 0% |
| Group B (clothianidin + PD SACP) | 99.5% | 99.7% | 99.5% | 99% | 97% | 88% | 87% | 82% |

*bef. tr. = before treatment, aft. tr. = after treatment

The invention claimed is:

1. A suspension concentrate composition comprising
at least one insecticide,
a nonionic and/or ionic dispersant, and
a grafted aqueous polymer dispersion,
wherein the insecticide is deltamethrin or beta-cyfluthrin,
wherein the polymer dispersion is prepared by radical-initiated emulsion copolymerization in the presence of a hydrocolloid comprising starch as a grafting base, of a monomer mixture comprising
a) 30 to 60% by weight, based on the monomer mixture weight, of at least one styrene or substituted styrene,
(b) 60 to 30% by weight, based on the monomer mixture weight, of at least one C1-C4-alkyl (meth)acrylate, and
(c) 0 to 10% by weight, based on the monomer mixture weight, of other ethylenically unsaturated copolymerizable monomers,
and wherein the starch (d) employed is 10 to 40% by weight of degraded starch with a molar weight $M_n$=500 to 10 000, the total of (a)+(b)+(c)+(d) being 100%, and the radical-initiator employed for the radical-initiated emulsion polymerization is a graft-active, water-soluble redox system,
and wherein the polymer dispersion after drying has a glass transition temperature of 40° C. to 80° C.

2. The composition according to claim 1, wherein the polymer dispersion at a concentration of 0.025% by weight in demineralized water at a wavelength of 535 nm and a path length of 1 cm has an absorbance of not more than 2.0.

3. A method for controlling pests comprising employing the composition according to claim 1 for controlling pests.

4. The method according to claim 3 comprising treating a surface with a deposition rate of 1.0 mg/m² to 2000 mg/m² polymer based on solids content.

5. An aqueous grafted polymer dispersion suitable for use in a pesticide which,
in demineralized water at a concentration of 0.025% by weight based on the solids content, has an absorbance, measured in a 1 cm cell at 535 nm, of <2.0 and
after drying has a glass transition temperature of 40° C. to 800° C.,
wherein the pesticide is deltamethrin or beta-cyfluthrin,
wherein the polymer dispersion is prepared by radical-initiated emulsion copolymerization in the presence of a hydrocolloid comprising starch as a grafting base, of a monomer mixture comprising
a) 30 to 60% by weight, based on the monomer mixture weight, of at least one styrene or substituted styrene,
(b) 60 to 30% by weight, based on the monomer mixture weight, of at least one C1-C4-alkyl (meth)acrylate, and
(c) 0 to 10% by weight, based on the monomer mixture weight, of other ethylenically unsaturated copolymerizable monomers,
and wherein the starch (d) employed is 10 to 40% by weight of degraded starch with a molar weight $M_n$=500 to 10 000, the total of (a)+(b)+(c)+(d) being 100%, and the radical-initiator employed for the radical-initiated emulsion polymerization is a graft-active, water-soluble redox system.

6. A medicament comprising a composition according to claim 1 suitable for controlling ectoparasites in animals.

7. A method of extending the efficacy of a pesticide comprising adding a grafted polymer dispersion to a composition comprising said pesticide prior to application, which polymer dispersion, at a concentration of 0.025% by weight in demineralized water at a wavelength of 535 nm and a path length of 1 cm, has an absorbance of less than 2.0,
wherein the insecticide is deltamethrin or beta-cyfluthrin,
wherein the polymer dispersion is prepared by radical-initiated emulsion copolymerization in the presence of a hydrocolloid comprising starch as a grafting base, of a monomer mixture comprising
a) 30 to 60% by weight, based on the monomer mixture weight, of at least one styrene or substituted styrene,
(b) 60 to 30% by weight, based on the monomer mixture weight, of at least one C1-C4-alkyl (meth)acrylate, and
(c) 0 to 10% by weight, based on the monomer mixture weight, of other ethylenically unsaturated copolymerizable monomers,
and wherein the starch (d) employed is 10 to 40% by weight of degraded starch with a molar weight $M_n$=500 to 10 000, the total of (a)+(b)+(c)+(d) being 100%, and the radical-initiator employed for the radical-initiated emulsion polymerization is a graft-active, water-soluble redox system.

8. The composition of claim 1, wherein said at least one insecticide is deltamethrin.

9. The composition of claim 1, wherein said insecticide is partially embedded on a surface by a layer of said polymer dispersion formed between said insecticide and said surface.

10. The composition of claim 1, wherein said composition demonstrates longer-lasting insecticidal activity on both porous and non-porous surfaces than an identical composition without said polymer dispersion.

11. The composition of claim 1, wherein said composition demonstrates longer-lasting insecticidal activity on an animal than an identical composition without said polymer dispersion.

12. The method according to claim 3 comprising treating a surface with a deposition rate of 5 mg/m² to 200 mg/m² polymer based on solids content.

13. The composition of claim 1, wherein the C1-C4-alkyl (meth)acrylate comprises n-butyl acrylate and t-butyl acrylate.

14. The composition according to claim 1, wherein in concentrated formulations, the amount of insecticide is between 0.01 to 40% by weight, and the amount polymer dispersion is between 1 and 50% by weight.

15. The composition according to claim 1, wherein in ready-to-use compositions, the amount of insecticide is between 0.001 and 0.5% by weight, and the amount of polymer dispersion is between 0.002 and 1% by weight.

16. The composition of claim 1, wherein said at least one insecticide is beta-cyfluthrin.

* * * * *